United States Patent [19]

Hull et al.

[11] Patent Number: 5,893,840

[45] Date of Patent: *Apr. 13, 1999

[54] RELEASABLE MICROCAPSULES ON BALLOON CATHETERS

[75] Inventors: Vincent W. Hull, Fridley; Robert S. Schwartz, Rochester; Michael Dror, Edina, all of Minn.

[73] Assignee: Medtronic, Inc., Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/637,112

[22] Filed: Apr. 24, 1996

Related U.S. Application Data

[60] Continuation of application No. 07/233,145, Apr. 25, 1994, abandoned, which is a division of application No. 07/853,667, Mar. 19, 1992, abandoned, which is a continuation-in-part of application No. 07/637,436, Jan. 4, 1991, Pat. No. 5,102,402.

[51] Int. Cl.$^6$ ..................................................... A61M 29/00
[52] U.S. Cl. ............................ 604/96; 604/265; 606/194; 606/192
[58] Field of Search ..................... 604/96–101, 265, 604/266, 49, 52, 53; 606/191–196, 198, 108, 197; 128/898; 623/1, 11, 12, 66

[56] References Cited

U.S. PATENT DOCUMENTS

| Re. 31,873 | 4/1985 | Howes . |
| 3,086,525 | 4/1963 | Whitcomb . |
| 3,169,527 | 2/1965 | Sheridan . |
| 3,817,248 | 6/1974 | Buckles et al. . |
| 3,885,561 | 5/1975 | Cami . |
| 3,971,385 | 7/1976 | Corbett . |
| 4,417,576 | 11/1983 | Baran . |
| 4,423,725 | 1/1984 | Baran et al. . |
| 4,437,856 | 3/1984 | Valli . |
| 4,603,152 | 7/1986 | Laurin et al. . |
| 4,655,746 | 4/1987 | Daniels et al. . |
| 4,664,657 | 5/1987 | Williamitis et al. . |
| 4,714,460 | 12/1987 | Calderon . |
| 4,717,379 | 1/1988 | Ekholmer . |
| 4,769,013 | 9/1988 | Lorenz et al. . |
| 4,784,647 | 11/1988 | Gross . |
| 4,790,813 | 12/1988 | Kensey . |
| 4,839,175 | 6/1989 | Guo et al. . |
| 4,867,817 | 9/1989 | Kneafsey et al. . |
| 4,886,062 | 12/1989 | Wiktor ................................ 606/194 |
| 4,898,734 | 2/1990 | Mathiowitz et al. . |
| 4,900,303 | 2/1990 | Lemelson . |
| 4,913,683 | 4/1990 | Gregory . |
| 4,923,450 | 5/1990 | Maeda et al. . |

(List continued on next page.)

FOREIGN PATENT DOCUMENTS

| 5435036 | 10/1979 | Japan . |
| WO8912478 | 12/1989 | WIPO . |

OTHER PUBLICATIONS

"Direct Intraarterial Wall Injection of Microparticles Via a Catheter: A potential Drug Delivery Strategy Following Angiplasty", by Robert L Wilensky et al., published in Progress in Cardiology, Oct. 1991, pp. 1136–1140.

"Direct Intraarterial Wall Injection of Microparticles Via a Catheter: A potential Drug Delivery Strategy Following Angioplasty", by Robert L. Wilensky et al., published in Progress in Cardiology, Oct. 1981, pp. 1136–1140.

Primary Examiner—Ronald K. Stright, Jr
Attorney, Agent, or Firm—Daniel W. Latham; Harold R. Patton

[57] ABSTRACT

Balloon catheters are prepared to include body affecting chemicals within microcapsules on the exterior of the balloon either alone or with a stent. The coating releases from the balloon when the balloon is inflated into contact with the lumen to be treated. The device provides accurate placement of the dosage required at the location in need of treatment. A sheath may be employed over the balloon and microcapsules to prevent the microcapsules from being rubbed off during delivery through a body lumen. The catheters are especially useful in balloon angioplasty procedures.

2 Claims, 3 Drawing Sheets

U.S. PATENT DOCUMENTS

| | | |
|---|---|---|
| 4,968,307 | 11/1990 | Dake et al. . |
| 4,994,033 | 2/1991 | Shockey et al. . |
| 5,015,231 | 5/1991 | Keith et al. . |
| 5,049,130 | 9/1991 | Powell . |
| 5,049,131 | 9/1991 | Deuss . |
| 5,049,132 | 9/1991 | Shaffer et al. . |
| 5,073,365 | 12/1991 | Katz et al. . |
| 5,087,244 | 2/1992 | Wolinsky et al. . |
| 5,092,841 | 3/1992 | Spears ................. 606/194 |
| 5,092,877 | 3/1992 | Pinchuk . |
| 5,098,381 | 3/1992 | Schneider . |
| 5,102,402 | 4/1992 | Dror et al. . |
| 5,112,305 | 5/1992 | Barath et al. . |
| 5,120,322 | 6/1992 | Davis et al. . |
| 5,133,732 | 7/1992 | Wiktor ................. 606/192 |
| 5,135,484 | 8/1992 | Wright . |
| 5,135,516 | 8/1992 | Sahatjian et al. . |
| 5,171,217 | 12/1992 | March et al. . |
| 5,213,576 | 5/1993 | Abiuso et al. . |
| 5,226,430 | 7/1993 | Spears et al. . |
| 5,286,254 | 2/1994 | Shapland et al. . |
| 5,304,121 | 4/1994 | Sahatjian ................. 604/265 |
| 5,324,261 | 6/1994 | Amundson et al. . |
| 5,370,614 | 12/1994 | Amundson et al. . |
| 5,500,013 | 3/1996 | Buscemi et al. . |
| 5,554,119 | 9/1996 | Harrison et al. . |
| 5,558,642 | 9/1996 | Schweich, Jr. et al. . |

RELEASABLE MICROCAPSULES ON BALLOON CATHETERS

This is a continuation of application Ser. No. 08/233,145 filed Apr. 25, 1994, now abandoned, which is a divisional of Ser. No. 07/853,667 filed Mar. 19, 1992, now abandoned, which is a continuation-in-part of Ser. No. 07/637,436 filed Jan. 4, 1991, now U.S. Pat. No. 5,102,402.

BACKGROUND OF THE INVENTION

1. Field of the Invention

This invention relates to balloon catheters and more particularly to balloon angioplasty catheters having plaque-affecting compound releasably attached to a balloon.

2. Description of the Related Art

Dilatation balloons on catheters are well known in the art and are used to decrease the restriction caused by plaque within a vessel wall. Plaque varies greatly in consistency and may be anything from a soft fatty tissue to a harder calcified material. In either case, it is often desirable to do more than simply force a balloon against the plaque or other restriction in the hopes that any plaque and vessel wall may be, stretched to open the lumen more fully. Laser angioplasty uses lasers to vaporize the plaque at the stenosis.

Researchers are currently screening a number of drugs to limit or dissolve plaque. Unfortunately, such compositions have been difficult to apply directly where needed. Instead, such drugs tend to be applied systemically which essentially treats portions of the body which need no treatment. Also, such treatments mean that the dosage to the body must be quite high to insure that the area having a need for treatment will receive adequate drugs.

Researchers at the University of Chicago School of medicine incorporated a drug with magnetite particles in albumin solution and formed microcapsules 1.5 µm in diameter. The microcapsules were localized with the use of external magnetic fields. The local effects obtained matched those obtained with one hundred times as much drug given intravenously. J. Widder et al, *Adv. Pharm.* Chemother., 16, 213 (1979).

Concentrated heparin is delivered by a perforated balloon catheter in work by Wolinsky et al, as described in European Patent publication 0 383 429 of C. R. Bard, Inc. The drug is sprayed through minute holes in the balloon. Also see JACC Vol. 15, No. 2, February 1990:475–81 by Wolinsky et al. The assignee of the present invention has filed a patent application entitled "Intralumenal Drug Eluting Prosthesis", Ser. No. 07/486,580, filed Feb. 28, 1990, now abandoned which places a stent bearing drug at the location desired. Other attempts have involved an application of catheters having separated balloons and the introduction of the drug from an internal lumen of the catheter to the space formed between two inflated balloons. Obviously, this procedure requires the introduction of drug through a lumen within the catheter meaning that the volume of the drug is quite high. Also, if the plaque is badly fissured there will not be a complete seal between the two balloons and the drug will escape to other parts of the body through the vessel.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. Section 56(a) exists.

SUMMARY OF THE INVENTION

The invention provides means for placing plaque-affecting drugs or diagnostic materials exactly where it is needed, and only where it is needed. The invention allows the modification of any existing balloon catheter by applying drugs to the exterior of the balloon. The drug may be applied to the balloon in the form of microcapsules, polymer coated crystals, a drug or other reservoir-bearing drug which may be adhered permanently or temporarily to the balloon wall. The term "drug" as used herein refers to any agent or combination of agents that may affect the cells in the lumen, and includes diagnostic reagents.

Generally, the drug or other bioaffecting chemical is placed in a reservoir formed from a polymer which may be coated over the wall of the balloon. The polymer may be attached to the balloon by solvent bonding, adhesives, welding or the like. If the balloon has folds, corrugations, cusps or the like, the polymer may be coated on to the balloon, inflated such that when the balloon deflates, large portions of the closed folds or other convolutions will entrap drug-containing polymer. Thus, the microcapsules may be mechanically trapped to the exterior of the balloon without the use of adhesives. The catheter is then guided to the appropriate position using conventional techniques. When the balloon is inflated, it expands greatly causing the polymer-coated drug to come in contact with the plaque or vessel wall and especially fills any fissures which may be present in the plaque. The drug in highly concentrated form is then placed exactly where it is needed. The actual dosage is extremely small since it must only effect the affected region.

The invention allows a physician to determine the type and extent of the plaque and then either use a previously coated catheter or to coat an uncoated catheter with a drug or drugs desired at the dosage indicated. Any balloon catheter may be modified by placing a coating of drug bearing reservoirs onto the wall of the balloon prior to its use. Since far less pressure is needed to rupture a microcapsule than to expand a lumen, the balloon may be of a simpler construction than with existing angioplasty balloons.

In yet another aspect of the invention, to protect the microcapsules from being rubbed off of the balloon during the movement of the microcapsules coated balloon through the body lumen, a protective sheath can be applied over the balloon and microcapsules. The sheath then is retracted or opened when the balloon reaches a desired location in the body lumen, thereby allowing the balloon to be expanded into contact with the lumen wall and to thereby deliver the microcapsules to the lumen wall.

In yet another aspect of the invention, the balloon with microcapsules can also be combined with a stent in order to provide additional support for the body lumen being treated. For example, the stent can be a stent made in whole or part from a bioabsorbable polymer and embedded microcapsules. The stent can be placed on the balloon and expanded into contact with the body lumen wall, thereby providing a drug eluting support structure for the lumen wall.

BRIEF DESCRIPTION OF THE DRAWINGS

Described with specific reference being made to the drawings in which.

DESCRIPTION OF THE PREFERRED EMBODIMENTS

Drugs

Figure 1:
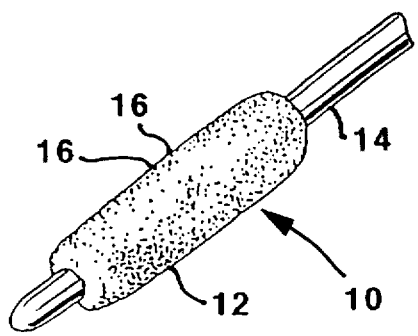
FIG. 1 is a fragmentary perspective view of an uninflated catheter of the invention.

The drugs in the microcapsules may be of any type which would be useful in treating the lumen. By treatment, the invention also contemplates diagnostic techniques which will aid in later treatment. Thus "drugs" may include diagnostic agents such as radiopaque compounds that allow the vessel to be visualized by fluoroscopy or similar methods. A dye within the microcapsules would be visible on the plaque after release by fluoroscopy. Also, the balloon itself may indicate the degree of blockage since only those microcapsules abutting against hard blockage will rupture, giving a reverse image of the blocked lumen.

In order to prevent restenosis in blood vessels, migration and subsequent proliferation of smooth muscle cells must be checked. Platelet aggregation and adhesion can be controlled with antiplatelets, antithrombotics and anticoagulants. Growth factor and receptor blockers and antagonists may be used to limit the normal repair response. The drugs may be in a liquid, semi-liquid or crystalline form. If crystalline, the crystals, coated or uncoated, may function as microcapsules and be dusted or loosely adhered to the balloon wall.

Microcapsules

The microcapsules usable in the invention may be fabricated in accordance with any of the known methods for preparing microcapsules. U.S. Pat. Nos. 4,897,268, 4,675,189, 4,542,025, 4,530,840, 4,389,330, 4,622,244, 4,464,317 and 4,943,449, the disclosures of which are incorporated herein by reference, describe methods for forming microcapsules which would be suitable for this invention.

Microencapsulation is also described in Encyclopedia of Poly. Sci, & Eng, Vol. 9, by Curt Thies at pages 724-745 (2nd Ed. 1985) and in a chapter on Microencapsulation by R. Sparks in Kirk-Othmer, pages 470-493, Vol. 15 (3rd Ed).

The microcapsules of the invention, may either be rupturable to release their contents or may be degradable such that they will open when left against the lumen walls.

The capsules may release their contents through diffusion or by rupturing due to the application of ultrasonic forces. Many of the current applications for microcapsules require them to be easily ruptured under pressure, as in the case of carbonless copy paper. Typically, the microcapsules would be on the order of from to 100 microns in diameter. The drug within the microcapsule will typically be in solution or otherwise dispersed throughout the polymer of the microcapsule. However, since it is possible to microencapsulate crystals, drug crystals may be employed.

In such cases, the microcapsule may present sharp angles which will easily become embedded and fixed to the lumen wall when the balloon is inflated.

Brittle microcapsules will release their contents when the balloon is inflated since the expanding membrane of the balloon causes their walls to expand. In this manner, the fracture is inflation dependent, not time or pressure dependent. As the balloon inflates, encapsulated crystals tend to break free from their attachment to the balloon wall as it stretches. A typical dilatation catheter balloon may expand in circumference by 500% which stresses the attachment points to the microcapsules.

When referred to herein, microcapsule shall include microspheres. The release mechanisms from the microcapsules may include any of the existing release mechanisms, such as those described by Robert Langer in "New Methods of Drug Delivery", Science, Vol. 249, Sep. 28, 1990, pp. 527:1533.

Catheter Formation

The dilatation catheters of the invention may include any dilatation catheter to which microcapsules are applied. The catheter need not be a dilation catheter as such. Any balloon catheter, whether capable of use in angioplasty or not may be employed. Since much lower pressures may be needed to release the drug, the balloon may be formed from a simple elastomer rather than a polyethylene. The microcapsules may be added in an original equipment manufacturing step or may be applied to previously formed catheters by spray coating or dipping the catheters to add microcapsules. A physician can thereby customize a catheter selected by adding a mixture of microcapsules containing the drugs needed to affect the lumen.

Figure 3:
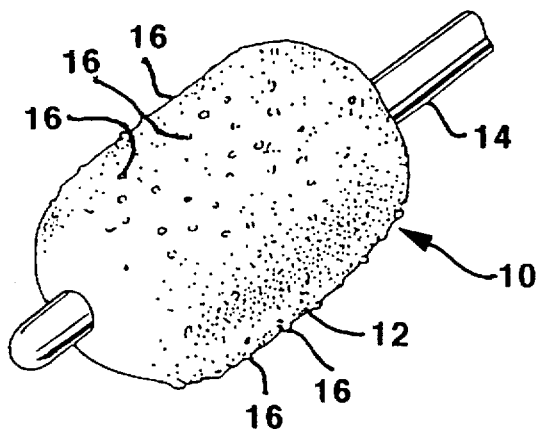
FIG. 3 is a view similar to that of FIG. 1 showing the balloon inflated.

FIGS. 1 and 3 show a portion of a typical balloon catheter including a balloon 12. The balloon 12 is secured to the distal portion of a catheter tube 14 in a location overlying one or more apertures in the tube 14. The catheter may include guiding means, insertion means or laser angioplasty means.

The balloon includes a covering of microcapsules 16 on its exterior surface. FIGS. 4 through 10 which are discussed below, provide details on the microcapsule attachment and release.

Figure 2:
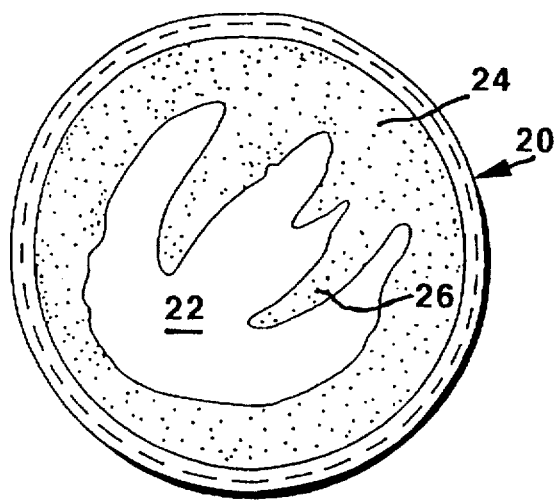
FIG. 2 is an enlarged transverse section of a body lumen in need of treatment.

The catheter 10 is inserted into the cardiovascular system until the balloon 12 is located at the lesion site. A typical site is shown in FIG. 2. In that figure, a cross-section of a vessel 20 needing treatment is shown. The interior 22 of the vessel is largely occluded by plaque 24 which may include intimal flaps 26. The balloon 12 is inflated by the addition of pressurized fluid which unfolds the balloon presenting a relatively smooth outer surface or working profile for exerting radially outward forces on the plaque. This accomplishes vessel dilation which reduces the degree of occlusion by the plaque.

Unfortunately, the application of pressure against the vessel interior does not end the possibility of restenosis, or re-occlusion of the vessel at the treatment site. The balloon catheters 10 of the invention apply drugs or other agents directly to the vessel wall where needed. The microcapsules 16 which carry the active agents are placed directly against the plaque or other tissue of the vessel wall by the inflation of the balloon. The microcapsules release their contents through dilation breakage due to physical contact or ultrasound, degradation and the like. Where intimal flaps are present, the invention allows the placement of many microcapsules within the fissures that are normally difficult to reach and treat.

The catheters of the invention may also be prepared by inflating the balloon and dusting microcapsules over the balloon. When the balloon deflates the microcapsules remain attached in the pores of the balloon wall.

Protective Sheath

To protect the microcapsules from being rubbed off of the balloon during the movement of the microcapsule coated balloon through the body lumen, a protective sheath can be applied over the balloon and microcapsules. The sheath is then retracted or opened when the balloon reaches a desired location, thereby allowing the balloon to be expanded into contact with the body lumen and to deliver the microcapsules to the lumen wall.

Figure 11:
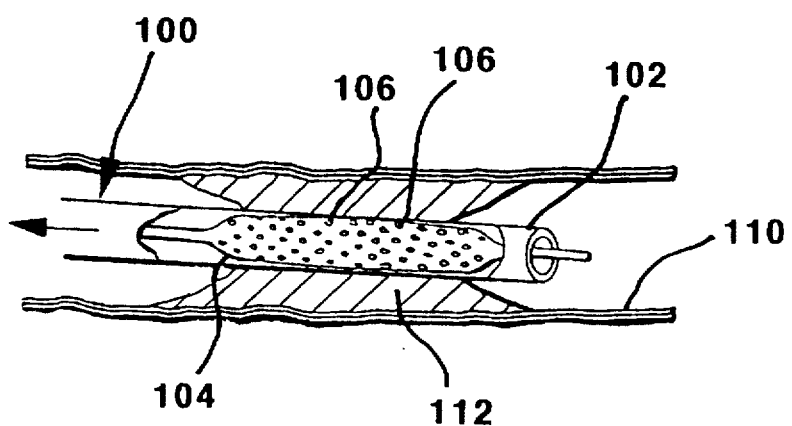
FIGS. 11-12 are longitudinal sectional views of a body lumen requiring treatment and the deployment of a sheathed microcapsule balloon.

For example, the sheath can be an integral part of the delivery catheter into which the balloon (and its included microcapsules) is axially inserted. Such a catheter is shown in longitudinal section in FIG. 11. The catheter includes a sheath 102 axially aligned with and encompassing the collapsed balloon 104. The microcapsules 106 are on the balloon 104 as described above and are also encompassed by the sheath 102. The catheter 100 is in a body lumen 110 depicted in cross-section at the site of a closure or restriction 112.

Figure 12:
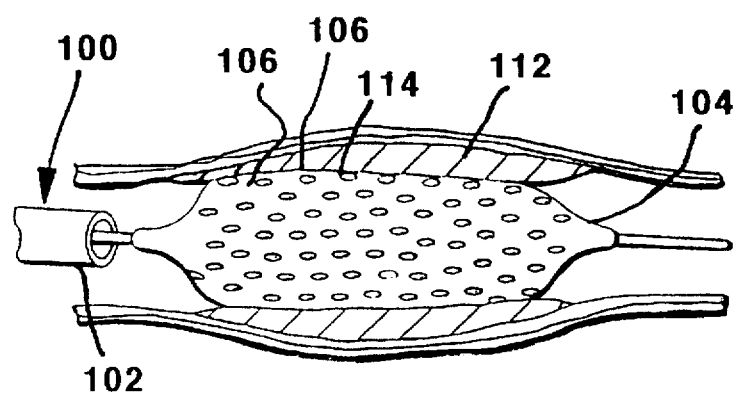

Referring also now to FIG. 12, when the catheter 100 and balloon 104 are into the closure or restriction 112, the sheath 102 is retracted, allowing the balloon 104 and microcapsules 106 to expand into contact with the lumen wall 114 at the point of closure or restriction 112. The retraction of the sheath 102 can be accomplished from the proximal end of the catheter by retracting a catheter element (not shown) which is integral with the sheath 102 which extends from the proximal end of the catheter to the sheath 102. The balloon 104 and microcapsules 106 are then delivered to the lumen wall 114 at the point of closure or restriction 112 as described herein. Other sheath configurations can also be used in the present invention including sheaths with perforations or openings which expand or separate as the balloon is expanded to open the sheath and thereby release the microcapsules into contact with the body lumen.

For example, the sheath can be a thin, elastic mesh material which when applied over the balloon and microcapsules can protect the microcapsules during delivery through the body lumen and upon inflation the balloon will allow the microcapsules to be delivered through enlarged mesh openings to the body lumen.

Stent

In yet another aspect of the invention, the balloon with microcapsules can also be combined with a stent in order to provide additional support for the body lumen being treated. For example, the stent can be a stent made in whole or in part from a biostable or bioabsorbable polymer in which the microcapsules are embedded. The stent can be placed on the balloon and expanded into contact with the body lumen wall, thereby providing a drug eluting support structure for the lumen wall.

Figure 13:
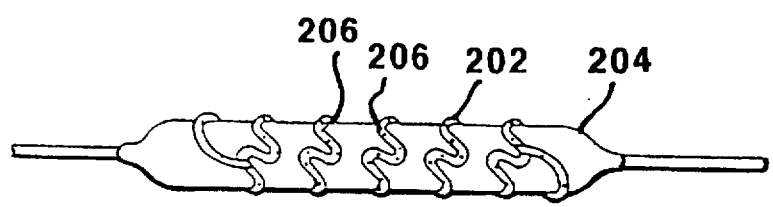
FIG. 13 is a elevational view of a balloon with stent and microcapsules thereon.

Referring now to FIG. 13, the stent 202 is shown mounted on the balloon 204 and is shown with included microcapsules 206. The stent 202 can be made by a variety of methods. In one such method, a metallic wire is formed into a stent substantially as disclosed in U.S. Pat. No. 4,886,062 issued to Wiktor, which is incorporated herein by reference. The metallic stent is then dip coated into a solution of the bioabsorbable polymer and, while still tacky, coated with microcapsules. Successive dip coatings and microcapsule coatings can provide a stent 202 with multiple layers of included microcapsules 206. By varying the amount of microcapsules in each layer or by varying the drugs contained in the microcapsules of the various coatings, a drug eluting structure can be established which, when in contact with a body lumen can elute drugs at a desired rate and amount and which can also elute and deliver drugs sequentially to the body lumen. The polymer can be, for example, the known synthetic bioabsorbable materials such as poly-l-lactic acid/polygycolic acid, polyanhydride and polyphosphate ester or natural bioabsorbable materials such as fibrin. The stent so made can be engaged with a balloon and delivered to the lumen wall at the site of a closure or restriction, all in a conventional manner.

Figure 14:
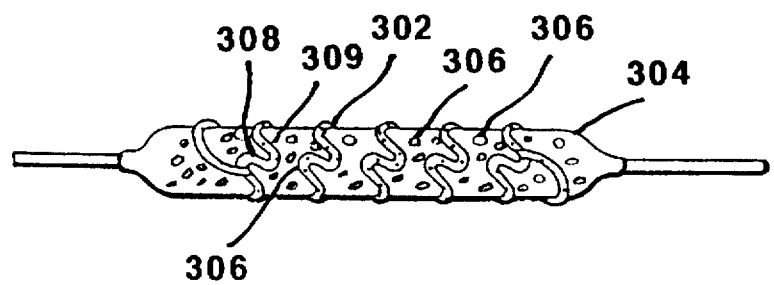
FIG. 14 is a elevation view of a balloon with stent and microcapsules thereon.

The combination of a stent with microcapsules and balloon can also be made in many other ways in the present invention. For example, as shown in FIG. 14 a conventional metal stent 302 can be engaged with a balloon 304 conventionally followed by application of microcapsules 306 to the combined balloon 304 and stent 302. Or, a metallic stent 302 without microcapsules but which as a substantially open structure such as that disclosed in FIG. 14 and shown and described more fully in the Wiktor U.S. Pat. No. 4,886,062 including zig-zags 306 taking a generally longitudinal direction 308 and then reversing their direction 309 and lying flat such that the zig-zags 306 open as the stent 302 is expanded can be applied over a balloon 304 with microcapsules 306 applied to the balloon 304 as disclosed herein. Or, the stent 302 and balloon can be coated with microcapsules 306 individually and combined for delivery to the body lumen.

Treatment

The dilatation catheters of the invention are used following the routine catheterization procedures. However, due to the presence of the microcapsules, when the balloon is inflated microcapsules and the drugs contained therewithin are delivered to the lumen wall, especially to any fissured areas at the site being treated.

Figure 4:
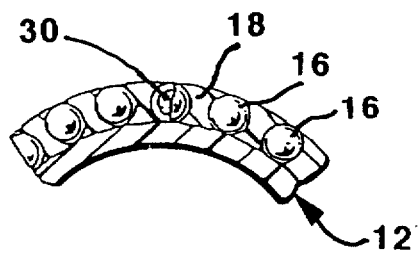
FIG. 4 is a greatly enlarged fragmentary section thereof as seen in FIG. 1.

FIG. 4 shows a fragment of the balloon 12 of FIG. 1. The balloon 12 is deflated in the Figure and traps the microcapsules 16 within a layer of adhesive 18. Although described as adhesive, layer 18 may simply be a portion of the balloon wall as a result of solvent bonding which overlays the microcapsules 16. One of the capsules 16 is shown in section to depict the interior filled with a liquid, semi-liquid or even crystalline agent 30. As shown, the microcapsules are firmly attached to the body of the deflated balloon 12.

Figure 5:
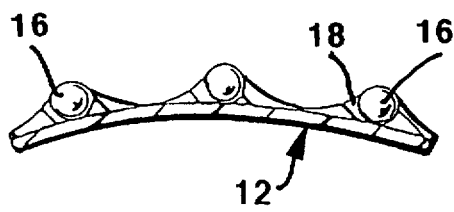
FIG. 5 is a greatly enlarged fragmentary section thereof as seen in FIG. 3.
Figure 6:
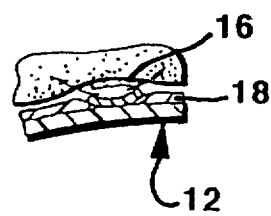
FIG. 6 is a greatly enlarged fragmentary section thereof showing dynamic mechanical function of the preferred form of the invention.

In contrast, FIG. 5 is a fragment of the inflated balloon 12 of FIG. 3 showing that inflation greatly stretches the balloon and adhesive 18 which exposes the microcapsules 16. The microcapsules are thus in a position that their contact with the vessel wall will cause them to release their contents to the cells of the vessel wall. Brittle microcapsules will rupture due to the stretching of the adhesive and not by the pressure of the balloon to the vessel wall. As the adhesive stretches it applies a force to the brittle microcapsules which causes them to rupture. FIG. 6 depicts the rupturing of a microcapsule 16. The agent inside is thus released directly against the cells of the vessel interior.

The amount of drug needed to treat the cells at a specific site in a vessel lumen is quite small. The microcapsules can easily carry the amount of cell affecting agents to the treatment site. A lower dosage is thus possible by the invention as well as a means to limit the possibly undesired effects of the drug on other areas of the body.

Figure 7:
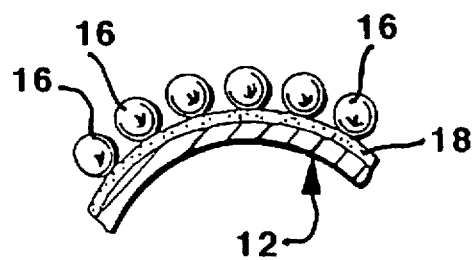
FIG. 7 is a greatly enlarged fragmentary section thereof showing a first alternate form of the invention.

FIG. 7 shows an alternative form of the invention in which the microcapsules are attached to the balloon 12 by a thin layer of adhesive 18 in contrast to that shown in FIG. 4. In this form, the microcapsules may simply break free from the limited amount of adhesive allowing them to be pressed into placement where desired quite readily. The microcapsules of FIG. 7 may be made to release their contents over time after being embedded into the tissue of the vessel wall as shown FIG. 9. This is in contrast to having the microcapsule break upon contact with the vessel wall.

Figure 8:
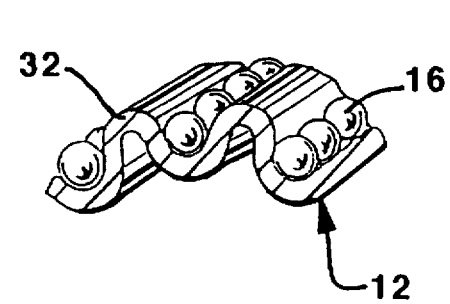
FIG. 8 is a greatly enlarged fragmentary pictorial detail of a second alternate form of the invention.
Figure 9:
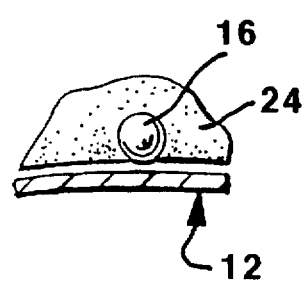
FIG. 9 is a greatly enlarged fragmentary section thereof showing dynamic mechanical function of a third alternate embodiment.
Figure 10:
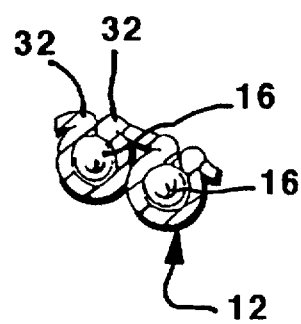
FIG. 10 is a greatly enlarged fragmentary section view thereof showing yet another alternate form thereof.

FIGS. 8 and 10 show that the microcapsules 16 of the invention may simply be held in place mechanically between any folds 32, corrugations, cusps or the like. Such are employed to carry the microcapsules without the need to attach the capsules by adhesive, welding or the like. As the balloon 12 inflates, the folds 32 are eliminated which expels the microcapsules into the treatment site.

The drawing of FIG. 10 shows that the balloon may be formed with permanent pleats that have a memory. In such a case, it is possible to place microcapsules 16 within the folds formed by the pleats as shown in FIG. 10. The application of more fluid into the balloon causes the pleats to unfold releasing the microcapsules 16.

If no microcapsules are present, such a design allows for a biphasic response, that is, the balloon may be partially inflated to be "fixed" against the lumen wall and finally inflated to a higher pressure where the lumen may be stretched.

While this invention may be embodied in many different forms, they are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed:

1. In a catheter of the type comprising a catheter body and a balloon positioned along the length of the catheter body, said catheter including means for remotely inflating and deflating said balloon; the improvement comprising:
   a. a plurality of microcapsules applied to the exterior of said balloon, each of said microcapsules carrying a drug or combination of drugs for treatment or diagnostics within a body lumen wherein the microcapsules are attached to the balloon by an adhesive which stretches and ruptures the microcapsules as the balloon expands; and
   b. a stent on the exterior of said balloon, the stent comprising a plurality of elements forming a hollow cylinder, the elements spaced apart along the cylinder with each of the elements extending around the cylinder, and each of the elements having zig-zags therein taking a generally longitudinal direction along the cylinder and then reversing their direction and lying flat with respect to the cylinder such that the zig-zags open as the stent is expanded from a first diameter to a second, expanded diameter, exposing the balloon and applied microcapsules on the balloon between the elements for direct contact with a body lumen.

2. In a catheter of the type comprising a catheter body and a balloon positioned along the length of the catheter body, said catheter including means for remotely inflating and deflating said balloon; the improvement comprising:
   a. a plurality of microcapsules applied to the exterior of said balloon, each of said microcapsules carrying a drug or combination of drugs for treatment or diagnostics within a body lumen which rupture under applied pressure to release the drug or combination of drugs for treatment or diagnostics wherein the microcapsules are attached to the balloon by an adhesive which stretches and ruptures the microcapsules as the balloon expands; and
   b. a stent on the exterior of said balloon, the stent comprising a plurality of elements forming a hollow cylinder and which open as the stent is expanded from a first diameter to a second, expanded diameter, exposing the balloon and applied microcapsules on the balloon between the elements for direct contact with a body lumen.

* * * * *